United States Patent [19]
Okada et al.

[11] Patent Number: 5,496,561
[45] Date of Patent: Mar. 5, 1996

[54] CONTROLLED RELEASE-INITIATION AND CONTROLLED RELEASE-RATE PHARMACEUTICAL COMPOSITION

[75] Inventors: Minoru Okada; Kenji Ono; Shuichi Kasai; Akira Iwasa, all of Chiba, Japan

[73] Assignee: SS Pharmaceutical Co., Ltd., Tokyo, Japan

[21] Appl. No.: 294,052

[22] Filed: Aug. 24, 1994

[30] Foreign Application Priority Data

Aug. 25, 1993 [JP] Japan .................... 5-210453

[51] Int. Cl.$^6$ .................... A61K 9/24; A61K 9/32
[52] U.S. Cl. .................... 424/480; 424/461; 424/462; 424/482; 424/494; 424/495; 424/497
[58] Field of Search .................... 424/458, 461, 424/462, 480, 482, 494, 5, 497

[56] References Cited

U.S. PATENT DOCUMENTS

| | | | |
|---|---|---|---|
| 4,859,469 | 8/1989 | Baudier et al. | 424/462 |
| 5,310,572 | 5/1994 | Woodard et al. | 427/3 |
| 5,346,542 | 9/1994 | Yosuke et al. | 106/194 |

FOREIGN PATENT DOCUMENTS

| | | | |
|---|---|---|---|
| 62-30709 | 2/1987 | Japan | A61K 9/16 |
| 4235123 | 8/1992 | Japan | A61K 9/58 |
| 4338323 | 11/1992 | Japan | A61K 9/52 |

*Primary Examiner*—Thurman K. Page
*Assistant Examiner*—James M. Spear
*Attorney, Agent, or Firm*—Sughrue, Mion, Zinn, Macpeak & Seas

[57] ABSTRACT

A controlled release-initiation and controlled release-rate pharmaceutical composition in which a drug-containing composition is coated with a membrane layer comprising a water insoluble high polymer and silicone. The starting time for the release of drugs from the controlled release-initiation and controlled release-rate pharmaceutical composition of this invention and the drug-releasing rate thereafter can be controlled at will.

22 Claims, 7 Drawing Sheets

United States Patent [19]
Okada et al.

[11] Patent Number: 5,496,561
[45] Date of Patent: Mar. 5, 1996

[54] CONTROLLED RELEASE-INITIATION AND CONTROLLED RELEASE-RATE PHARMACEUTICAL COMPOSITION

[75] Inventors: Minoru Okada; Kenji Ono; Shuichi Kasai; Akira Iwasa, all of Chiba, Japan

[73] Assignee: SS Pharmaceutical Co., Ltd., Tokyo, Japan

[21] Appl. No.: 294,052

[22] Filed: Aug. 24, 1994

[30] Foreign Application Priority Data

Aug. 25, 1993 [JP] Japan .................... 5-210453

[51] Int. Cl.$^6$ ................ A61K 9/24; A61K 9/32
[52] U.S. Cl. ............ 424/480; 424/461; 424/462; 424/482; 424/494; 424/495; 424/497
[58] Field of Search .................... 424/458, 461, 424/462, 480, 482, 494, 5, 497

[56] References Cited

U.S. PATENT DOCUMENTS 4,859,469  8/1989  Baudier et al. .................. 424/462
5,310,572  5/1994  Woodard et al. ................. 427/3
5,346,542  9/1994  Yosuke et al. .................. 106/194

FOREIGN PATENT DOCUMENTS 62-30709   2/1987  Japan ................. A61K 9/16
4235123    8/1992  Japan ................. A61K 9/58
4338323   11/1992  Japan ................. A61K 9/52

*Primary Examiner*—Thurman K. Page
*Assistant Examiner*—James M. Spear
*Attorney, Agent, or Firm*—Sughrue, Mion, Zinn, Macpeak & Seas

[57] ABSTRACT

A controlled release-initiation and controlled release-rate pharmaceutical composition in which a drug-containing composition is coated with a membrane layer comprising a water insoluble high polymer and silicone. The starting time for the release of drugs from the controlled release-initiation and controlled release-rate pharmaceutical composition of this invention and the drug-releasing rate thereafter can be controlled at will.

22 Claims, 7 Drawing Sheets

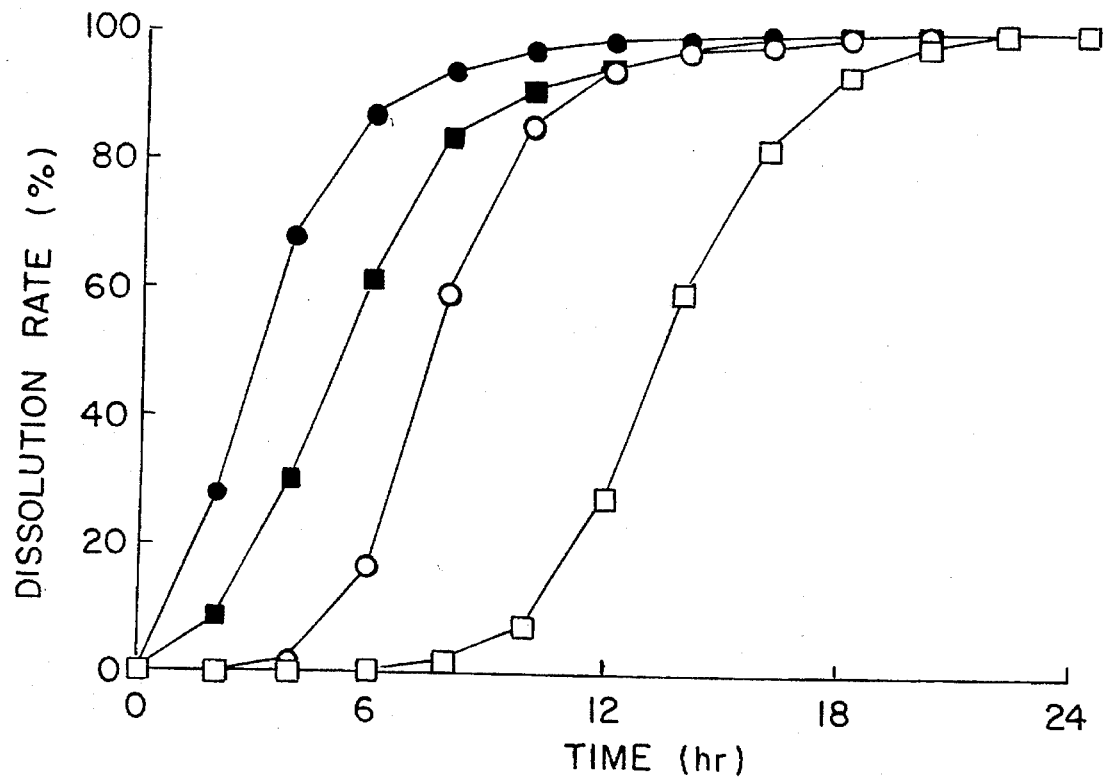

5,496,561

CONTROLLED RELEASE-INITIATION AND CONTROLLED RELEASE-RATE PHARMACEUTICAL COMPOSITION

FIELD OF THE INVENTION

This invention relates to a controlled release-initiation and controlled release-rate pharmaceutical composition in which the starting time of the release of a drug from a preparation and the releasing rate of the drug after commencement of its release can be controlled at will.

BACKGROUND OF THE INVENTION

When a pharmaceutical composition is applied to patients, it is necessary to guarantee its efficacy and safety, as well as its specificity corresponding to each purpose.

Because of this, great concern has been directed toward the development of a system in which a pharmaceutical composition is designed in such a dosage form that a drug of interest is delivered to a target site for a necessary period of time in a required amount.

In order to satisfy such a requirement, sustained release preparations which can give prolonged duration of action of a drug by controlling the releasing rate of the drug from the preparation have already been developed and put into practical use. In addition, other types of pharmaceutical compositions which can control commencement of the release of drugs have been proposed in recent years, such as a preparation in which a drug is released when the coat membrane of the preparation is disrupted due to swelling of a water swelling material (JP-A-62-30709 (corresponding to U.S. Pat. No. 4,871,549) and JP-A-4-338323; the term "JP-A" as used herein means an "unexamined published Japanese patent application"), a preparation in which a water repellent salt such as magnesium stearate, calcium stearate or the like fatty acid metal salt and an acrylic polymer are used in its coat membrane in order to give the preparation a lag time before the release of its ingredients (JP-A-4-235123 (corresponding to U.S. Pat. No. 5,137,733)) and a preparation in which mutual interaction between Eudragit RS (manufactured by Rohm Pharma GMBH) and an organic acid is applied (Abstract of Papers, 7th Annual Meeting of The Japanese Society of Pharmacy, p.84, 1991).

However, since drugs are produced with various purposes, development of a pharmaceutical composition having various drug release mechanisms which can respond to these purposes has been called for in the field of medicine.

SUMMARY OF THE INVENTION

In view of the above, an object of the present invention is to provide a pharmaceutical composition of new construction in which the starting time of the release of a drug from the preparation and the releasing rate of the drugs, after commencement of its release, can be controlled.

With the aim of overcoming the aforementioned problems involved in conventional compositions, the inventors of the present invention have conducted intensive studies and found that, when a drug-containing composition is coated with a membrane layer comprising a water insoluble high polymer and silicone, the starting time of the release of the drug can be controlled at will by changing the thickness of the membrane, and the releasing rate of the drug after commencement of its release can be controlled by changing the composition of the membrane. The present invention has been accomplished on the basis of these findings.

Thus, the present invention provides a controlled release-initiation and controlled release-rate pharmaceutical composition in which a drug-containing composition is coated with a membrane layer which contains a water insoluble high polymer and silicone.

BRIEF DESCRIPTION OF THE DRAWINGS

In FIG. 1, the curves, -o-, -□-, -●- and -■- stand for the results of Example 1-1, Example 1-2, Comparative Example 1-1 and Comparative Example 1-2, respectively.

FIG. 2 is a graph showing the results of tests of excretion into urine carried out in Test Example 2 using the controlled release-initiation and controlled release-rate pharmaceutical compositions obtained in Example 2. In FIG. 2, the curves, -o- and -□- stand for the results of Example 2-1 and Example 2-2, respectively.

FIG. 3 is a graph showing the results of dissolution tests carried out in Test Example 3 using the controlled release-initiation and controlled release-rate pharmaceutical compositions obtained in Example 3. In FIG. 3, the curves, -o-, -□- and -△- stand for the results of Example 3-1, Example 3-2 and Example 3-3, respectively.

In FIG. 4, the curves, -o-, -□- and -△- stand for the results of Example 4-1, Example 4-2 and Example 4-3, respectively.

In FIG. 5, the curves, -o-, -●-, -□- and -■- stand for the results of Example 5-1, Example 5-2, Example 5-3 and Example 5-4, respectively.

In FIG. 6, the curves, -o-, -□- and -△- stand for the results of Example 6-1, Example 6-2 and Example 6-3, respectively.

In FIG. 7, the curves, -o-, -□- and -△- stand for the results of Example 7-1, Example 7-2 and Example 7-3, respectively.

In FIG. 8, the curves, -o- and -□- stand for the results of Example 8-1 and Example 8-2, respectively.

In FIG. 9, the curve, -o- stands for the result of Example 9-1.

In FIG. 10, the curve, -o- stands for the result of Example 10-1.

In FIG. 11, the curve, -△- stands for the result of Example 11-1.

In FIG. 12, the curves, -o-, -□-, -■- and -▲- stand for the results of Example 1-1, Example 1-2, Comparative Example 2-1 and Comparative Example 2-2, respectively.

In FIG. 13, the curves, -o-, -□-, -■- and -▲- stand for the results of Example 1-1, Example 1-2, Comparative Example 3-1 and Comparative Example 3-2, respectively.

DETAILED DESCRIPTION OF THE INVENTION

Figure 1:
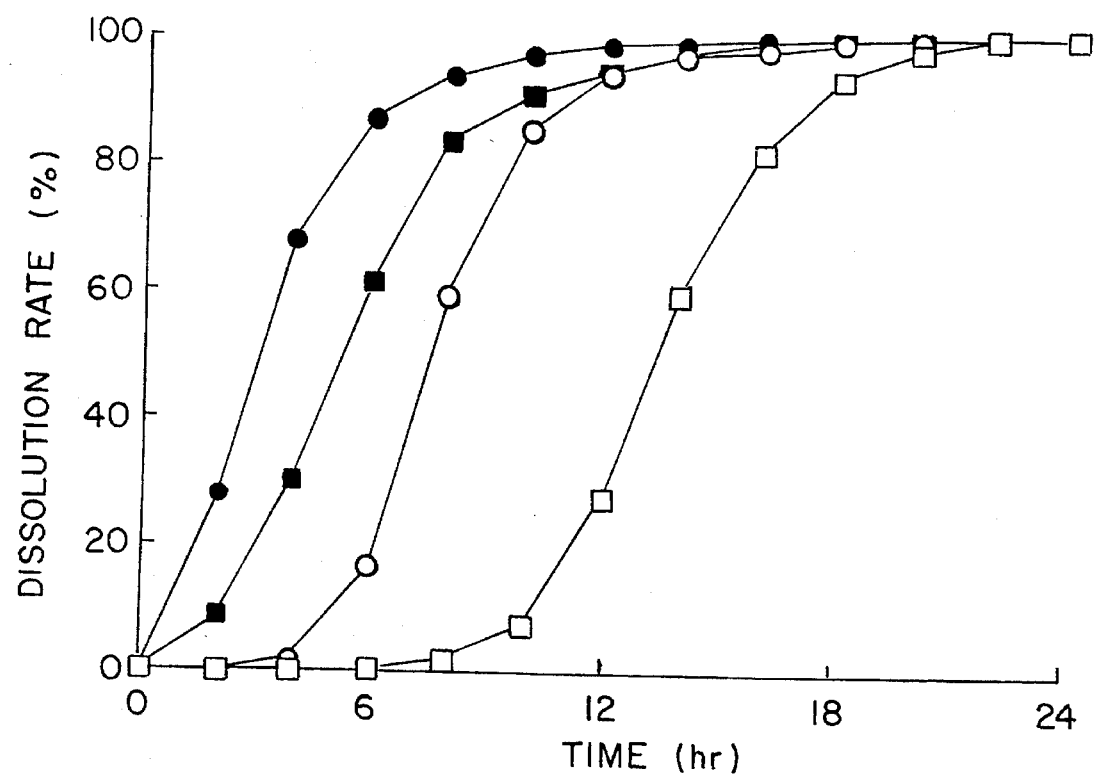
FIG. 1 is a graph showing the results of dissolution tests carried out in Test Example 1 using the controlled release-initiation and controlled release-rate pharmaceutical compositions obtained in Example 1 and comparative preparations obtained in Comparative Example 1.

In the pharmaceutical composition of the present invention, a composition containing a drug of interest forms the central core of the preparation, which may be used in the crystalline form of the drug as such or as any of the usually used solid dosage forms such as fine granules, granules, beads, tablets and the like, by mixing the drug with pharmaceutically acceptable carrier, such as fillers, binders, lubricants and the like. As occasion demands, the central core composition may be coated with a water soluble high polymer, an acid soluble high polymer, an enteric high polymer, a water insoluble high polymer, wax or the like. Though not particularly limited, typical examples of the drug to be contained in the central core composition include: drugs for use in the treatment of central nervous system related diseases, such as hypnotics, sedatives, antiepileptics, antipyretics, analgesics, antiinflammatory agents, stimulants, antihypnotics, antidinics, pyschoneurosis treating drags and the like; drugs for use in the treatment of pripheral nervous system related diseases, such as skeletal muscle relaxants, autonomic agents, autonomic blocking agents, preparations containing plant extracts and the like; drugs for use in the treatment of sensory organ related diseases, such as opthalmic preparations, otorhinologic preparations and the like; drugs for use in the treatment of circulatory organ related diseases, such as cardiotonics, antiarrhythmic agents, diuretics, hypotensive agents, capillary stabilizers, vasoconstrictors, vasodilators, antiarteriosclerosis agents and the like; drugs for use in the treatment of respiratory organ related diseases, such as respiratory stimulants, respiratory depressants, antitussives and the like; drugs for use in the treatment of digestive organ related diseases, such as peptic ulcer treating drugs, stomachics, digestants, antracids, cathartics, cholagogues, intestinal function controlling drugs and the like; hormones, such as hormones and hormone antagonists and the like; drugs for use in the treatment of urogenital organ and anus related diseases, such as urinary antiseptics oxytocics, urogenital drugs, hemorrhoid treating drugs, rectal preparations and the like; metabolic drugs, such as vitamins, aphrodisiacs, drugs for blood and body fluid, drugs for hepatic disease, antidotes, habitual intoxication treating agents, arthrifuges, enzyme preparations, antidiabetic drugs and the like; drugs for use in the treatment of tissue and cell function related diseases, such as cell activation drugs, antimalignant neoplastic agents and the like; drugs for use in the treatment of pathogenic organisms related diseases, such as antibiotics, chemotherapeutic agents, antiprotozoan agents, anthelmintics and the like; and narcotics such as alkaloid-type narcotics, non-alkaloid-type narcotics and the like.

Illustrative examples of the water insoluble high polymer to be used in the membrane layer of the pharmaceutical composition of the present invention include: water insoluble high polymers such as a terpolymer composed of ethyl acrylate, methyl methacrylate and ethyl trimethylammonium chloride methacrylate, ethyl cellulose and the like; and enteric high polymers which are insoluble under acidic condition, such as a copolymer composed of methacrylic acid and ethyl acrylate, a copolymer composed of methacrylic acid and methyl methacrylate, hydroxypropylmethylcellulose phthalate, hydroxypropylmethylcellulose acetate succinate, carboxymethylethyl cellulose, cellulose acetate phthalate and the like. Of these high polymers, the ethyl acrylate/methyl methacrylate/ethyl trimethylammonium chloride methacrylate terpolymer is particularly preferred, because it is most effective in prolonging the duration before drug-releasing while using (lag time) a lesser amount of coating. Preferably, the terpolymer has an ethyl acrylate:methyl methacrylate:ethyl trimethylammonium chloride methacrylate weight ratio of 1:2:0.1 to 1:2:0.2. Its commercially available examples include Eudragit RS and Eudragit RL (manufactured by Rohm Pharma GMBH).

The water insoluble high polymers exemplified above may be used alone or as a mixture of two or more, preferably in a range of from 20 to 95% by weight based on the total weight of the membrane layer.

The lag time and drug-releasing rate can be controlled by adding a small amount of a water soluble high polymer to the aforementioned water insoluble high polymer. Preferred examples of the water soluble high polymer include hydroxypropylmethyl cellulose, hydroxypropyl cellulose, polyvinyl pyrrolidone, polyethylene glycol and the like, preferably in a range of from 1 to 4% by weight based on the total weight of the membrane layer.

A silicone resin or a silicone oil, particularly dimethylpolysiloxane having a viscosity of 95 to 1,100 centistokes, is used preferably as the silicone to be contained in the membrane layer. The silicone may be contained in the membrane layer in an amount of preferably from 5 to 200% by weight, more preferably from 10 to 100% by weight, based on the aforementioned water insoluble high polymer.

It is preferable to add a silicone hold carrier to the membrane layer. Addition of a silicone hold carrier renders possible not only the inclusion of a large amount of silicone in the membrane layer but also the production of a highly stable pharmaceutical composition whose lag time before the release of a drug and the drug-releasing rate thereafter do not change even when a large amount of silicone is included in the membrane layer.

The silicone hold carrier is not particularly limited, provided that it can disperse and retain a liquid silicone in the water insoluble high polymer, but is selected preferably from talc, light anhydrous silicic acid, microcrystalline cellulose, starch and the like, of which light anhydrous silicic acid is particularly preferred. Preferably, the silicone hold carrier is used in the form of a fine powder having a large surface area. The silicone hold carrier is used in an amount of preferably from 0 to 200% by weight based on the silicone to be used.

A plasticizer may be further added to the membrane layer. Examples of useful plasticizers include triethyl citrate, triacetin, polyethylene glycol, castor oil, polyoxysorbitan monooleate, glycerine fatty acid ester and the like, which is preferably used in an amount of from 2 to 50% by weight based on the water insoluble high polymer.

The membrane layer to be coated may be used in an amount of generally from 2 to 200% by weight based on the central core weight, though it varies depending on the type of drug to be used, size and shape of the central core, intended lag time and release rate and composition of the membrane. In general, it is necessary to increase the coating quantity when a longer lag time is required, and the coating quantity also becomes large when the central core is small.

The pharmaceutical composition of the present invention can be produced by making central cores in the usual way and then coating each core with a membrane layer which contains a water insoluble high polymer and silicone.

Central cores can be produced by various known processes, such as a process in which fine granules and granules are produced by wet or dry granulation, a process in which these fine granules and granules are made into tablets by compression molding, a process in which tablets are produced by direct compression tableting, a process in which granules and beads are produced by rotary granulation, a process in which fine granules, granules and beads are produced by extrusion granulation and a process in which granules and beads are produced by extrusion granulation and subsequent treatment with Marumerizer (Fuji Paudal Co., Ltd.) or the like. Coating of the membrane layer may be effected by spray-coating the central cores with the membrane layer composition in a fluidized bed or a pan.

The controlled release-initiation and controlled release-rate pharmaceutical composition of the present invention may be further combined with an immediate-release preparation or with another inventive controlled release-initiation and controlled release-rate pharmaceutical composition having different lag times.

The controlled release-initiation and controlled release-rate pharmaceutical composition of the present invention once made into fine granules, granules, beads or tablets may be further made into a capsular dosage form by packing them into capsules, or the inventive fine granules, granules or beads may be made into tablets together with appropriate fillers, binders, lubricants and the like.

Since the controlled release-initiation and controlled release-rate pharmaceutical composition of the present invention can start the release of a drug from the preparation after a predetermined lag time, it can be made into sustained release preparations having various drug-releasing patterns by combining it with an immediate-release preparation or other preparations having different lag times. In addition, since the release of a drug can be set to a pulse type, the same blood concentration transition as the case of the administration of an immediate-release preparation several times a day can be obtained by once a day administration of the inventive preparation.

When a drug to which first-past effect exerts an adverse influence is applied in the form of a conventional sustained-release preparation, bioavailability thereof is extremely reduced. In accordance with the present invention, however, the decrease of bioavailability of such drug can be lessen because the inventive preparation can be set to a pulse type drug release pattern in which a drug of interest is released quickly at predetermined drug release starting times.

EXAMPLES

The following examples are provided to further illustrate the present invention. It is to be understood, however, that the examples are for purpose of illustration only and are not intended as a definition of the limits of the present invention. The term "%" as used herein means "% by weight".

EXAMPLE 1

A 1,500 g portion of trapidil was mixed with 100 g of hydroxypropyl cellulose and pulverized into fine powder. While spraying a solution of 20 g of hydroxypropyl cellulose dissolved in 380 g of ethyl alcohol, 1,280 g of the fine powder was applied to 400 g of Nonpareil 103 (spherical sugar having a particle size of 500 to 710 µm, manufactured by Freund Industrial Co., Ltd.) to effect rolling granulation, followed by 5 hours of drying at 60° C. The resulting granules were treated with screens and those which passed through a 12 mesh screen (sieve opening, 1.41 mm) but not a 32 mesh screen (sieve opening, 0.50 mm) were collected as uncoated granules.

Next, 1,000 g of the uncoated granules thus obtained were put in a fluidized bed coating apparatus and sprayed with a coating solution composed of 8% hydroxypropylmethyl cellulose, 2% talc, 45% ethyl alcohol and 45% purified water until a 10% increase in the weight of the uncoated granules was attained. In this way, central cores of the present invention were obtained.

Thereafter, 250 g of the thus obtained central cores were put in a fluidized bed coating apparatus and sprayed with a coating solution composed of 12% Eudragit RS, 8% dimethylpolysiloxane, 4% light anhydrous silicic acid, 1% glycerine fatty acid ester and 75% ethyl alcohol until a 60% (Example 1-1) or 90% (Example 1-2) increase in the weight of the granules was attained. In this way, the controlled release-initiation and controlled release-rate pharmaceutical compositions of the present invention were obtained in a dosage form of granules.

COMPARATIVE EXAMPLE 1

Central cores containing trapidil were obtained in the same manner as described in Example 1.

Next, 250 g of the thus obtained central cores were put in a fluidized bed coating apparatus and sprayed with a coating solution composed of 12% Eudragit RS, 4% light anhydrous silicic acid, 1% glycerine fatty acid ester and 83% ethyl alcohol until a 60% (Comparative Example 1-1) or a 90% (Comparative Example 1-2) increase in the weight of the granules was attained. In this way, the comparative and controlled release-rate pharmaceutical compositions were obtained in a dosage form of granules.

TEST EXAMPLE 1

The inventive controlled release-initiation and controlled release-rate pharmaceutical compositions 1-1 and 1-2 obtained in Example 1 and the silicone-free comparative pharmaceutical compositions 1-1 and 1-2 obtained in Comparative Example 1 were subjected to a trapidil dissolution test in accordance with the paddle method of The Pharmacopeia of Japonica, 12th revision, using phosphate buffer (pH 6.8) as a test solution. The results are shown in FIG. 1.

As is apparent from FIG. 1, in comparison with the comparative pharmaceutical compositions 1-1 and 1-2, the controlled release-initiation and controlled release-rate pharmaceutical compositions 1-1 and 1-2 of the present invention, having the same coating ratios, are capable of releasing trapidil after a lag time.

EXAMPLE 2

The inventive controlled release-initiation and controlled release-rate pharmaceutical compositions 1-1 and 1-2 obtained as granules in Example 1 were separately packed in hard capsules in such an amount that each capsule contained 150 mg of trapidil, thereby obtaining inventive controlled release-initiation and controlled release-rate pharmaceutical compositions 2-1 and 2-2 in a dosage form of capsules.

TEST EXAMPLE 2

Each of the controlled release-initiation and controlled release-rate pharmaceutical compositions 2-1 and 2-2 of the present invention obtained in Example 2 was administered to healthy male adults in a dose of one capsule per adult in order to measure excretion rate of trapidil into urine. The results are shown in FIG. 2.

As is apparent from FIG. 2, trapidil in the inventive controlled release-initiation and controlled release-rate pharmaceutical compositions 2-1 and 2-2 is excreted after 3 and 7 hours of lag time, respectively.

EXAMPLE 3

A 1,500 g portion of trapidil was mixed with 100 g of hydroxypropyl cellulose and pulverized into fine powder. While spraying a solution of 20 g of hydroxypropyl cellulose dissolved in 380 g of ethyl alcohol, 1,280 g of the fine powder was applied to 400 g of Nonpareil 103 (spherical sugar having a particle size of 500 to 710 μm, manufactured by Freund Industrial Co., Ltd.) to effect rolling granulation, followed by 5 hours of drying at 60° C. The resulting granules were treated with screens and those which passed through a 12 mesh screen (sieve opening, 1.41 mm) but not a 32 mesh screen (sieve opening, 0.50 mm) were collected as central cores of the present invention.

Thereafter, 250 g of the thus obtained central cores were put in a fluidized bed coating apparatus and sprayed with a coating solution composed of 6% Eudragit RS, 4% dimethylpolysiloxane, 2% light anhydrous silicic acid, 0.5% glycerine fatty acid ester and 87.5% ethyl alcohol until a 50% (Example 3-1), a 70% (Example 3-2) or a 90% (Example 3-3) increase in the weight of the granules was attained. In this way, the controlled release-initiation and controlled release-rate pharmaceutical compositions of the present invention were obtained.

TEST EXAMPLE 3

Dissolution of trapidil from the controlled release-initiation and controlled release-rate pharmaceutical compositions 3-1, 3-2 and 3-3 of the present invention obtained in Example 3 was measured in the same manner as described in Test Example 1. The results are shown in FIG. 3.

As is apparent from FIG. 3, each of the inventive pharmaceutical compositions releases trapidil quickly after a lag time, and the lag time becomes longer as the coating ratio increases. In addition, release of trapidil after lag time occurs at the same rate independent of the coating ratio.

EXAMPLE 4

Central cores containing trapidil were obtained in the same manner as described in Example 1.

Thereafter, 250 g of the thus obtained central cores were put in a fluidized bed coating apparatus and sprayed with a coating solution composed of 20% Eudragit RS, 4% dimethylpolysiloxane, 1% glycerine fatty acid ester and 75% ethyl alcohol until a 60% increase in the weight of the granules was attained, thereby obtaining a controlled release-initiation and controlled release-rate pharmaceutical compositions of the present invention (Example 4-1).

In the same manner, 250 g of the thus obtained central cores were put in a fluidized bed coating apparatus and sprayed with a coating solution composed of 14% Eudragit RS, 6% dimethylpolysiloxane, 3% light anhydrous silicic acid, 2% glycerine fatty acid ester and 75% ethyl alcohol until a 70% increase in the weight of the granules was attained, thereby obtaining the controlled release-initiation and controlled release-rate pharmaceutical compositions of the present invention (Example 4-2).

Also, 250 g of the thus obtained central cores were put in a fluidized bed coating apparatus and sprayed with a coating solution composed of 10% Eudragit RS, 9% dimethylpolysiloxane, 5% light anhydrous silicic acid, 1% glycerine fatty acid ester and 75% ethyl alcohol until a 100% increase in the weight of the granules was attained, thereby obtaining the controlled release-initiation and controlled release-rate pharmaceutical compositions of the present invention (Example 4-3).

TEST EXAMPLE 4

Dissolution of trapidil from the controlled release-initiation and controlled release-rate pharmaceutical compositions 4-1, 4-2 and 4-3 of the present invention obtained in Example 4 was measured in the same manner as described in Test Example 1. The results are shown in FIG. 4.

Figure 4:
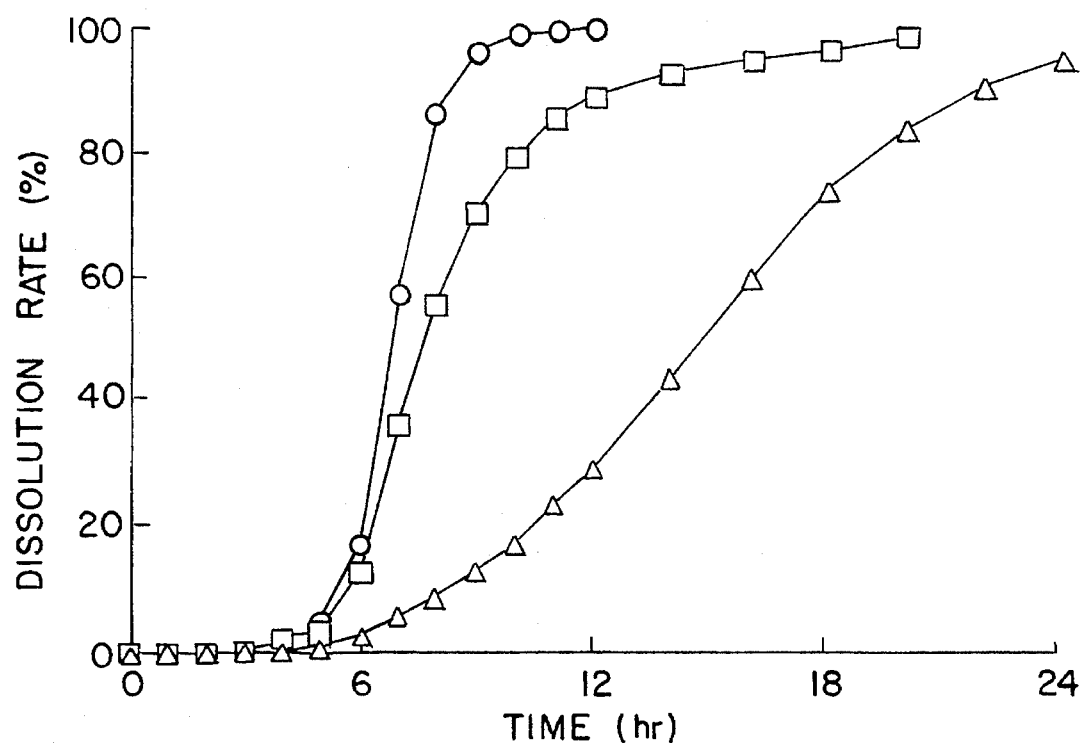
FIG. 4 is a graph showing the results of dissolution tests carried out in Test Example 4 using the controlled release-initiation and controlled release-rate pharmaceutical compositions obtained in Example 4.

As is apparent from FIG. 4, each of the inventive pharmaceutical compositions releases trapidil after a lag time, and the releasing rate of trapidil after the lag time can be controlled by changing the membrane composition.

EXAMPLE 5

Central cores containing trapidil were obtained in the same manner as described in Example 1.

Thereafter, 250 g of the thus obtained central cores were put in a fluidized bed coating apparatus and sprayed with a coating solution composed of 16% Eudragit RS, 4% dimethylpolysiloxane, 3% light anhydrous silicic acid, 2% glycerine fatty acid ester and 75% ethyl alcohol until a 50% (Example 5-1), an 80% (Example 5-2), a 110% (Example 5-3) or a 140% (Example 5-4) increase in the weight of the granules was attained. In this way, the controlled release-initiation and controlled release-rate pharmaceutical compositions of the present invention were obtained.

TEST EXAMPLE 5

Dissolution of trapidil from the controlled release-initiation and controlled release-rate pharmaceutical compositions 5-1, 5-2, 5-3 and 5-4 of the present invention obtained in Example 5 was measured in the same manner as described in Test Example 1. The results are shown in FIG. 5.

Figure 5:
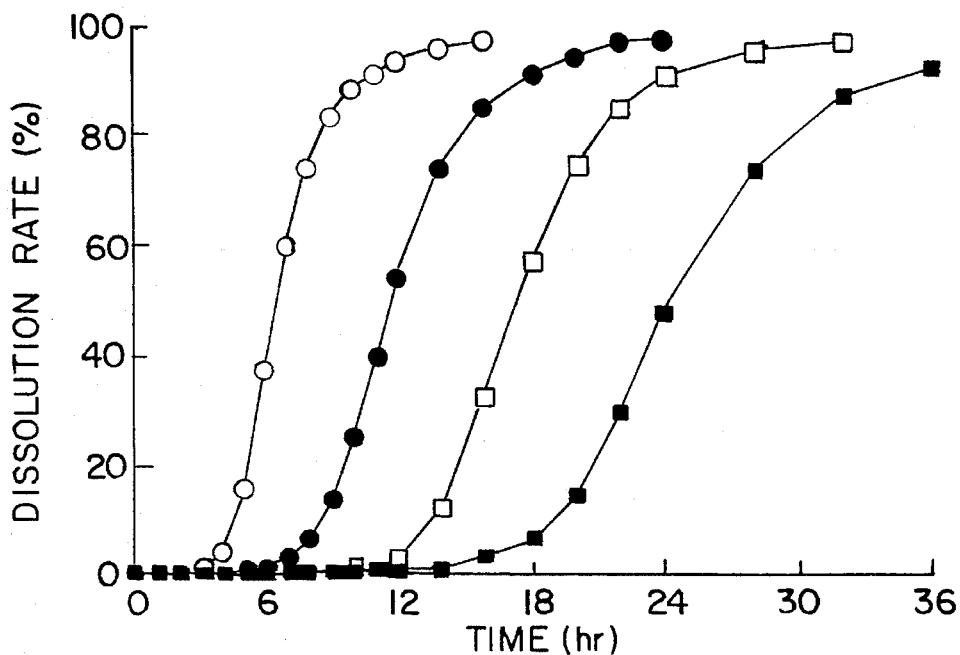
FIG. 5 is a graph showing the results of dissolution tests carried out in Test Example 5 using the controlled release-initiation and controlled release-rate pharmaceutical compositions obtained in Example 5.

As is apparent from FIG. 5, each of the inventive pharmaceutical compositions releases trapidil quickly after a lag time, and the lag time becomes longer as the coating ratio increases, thus showing that the release-starting time can be changed at will.

EXAMPLE 6

Central cores containing trapidil were obtained in the same manner as described in Example 1.

Thereafter, 250 g of the thus obtained central cores were put in a fluidized bed coating apparatus and sprayed with a coating solution composed of 12% Eudragit RL, 8% dimethylpolysiloxane, 4% light anhydrous silicic acid, 1% glycerine fatty acid ester and 75% ethyl alcohol until a 60% (Example 6-1), an 80% (Example 6-2) or a 100% (Example 6-3) increase in the weight of the granules was attained. In this way, the controlled release-initiation and controlled release-rate pharmaceutical compositions of the present invention were obtained.

TEST EXAMPLE 6

Dissolution of trapidil from the controlled release-initiation and controlled release-rate pharmaceutical compositions 6-1, 6-2 and 6-3 of the present invention obtained in Example 6 was measured in the same manner as described in Test Example 1. The results are shown in FIG. 6.

Figure 6:
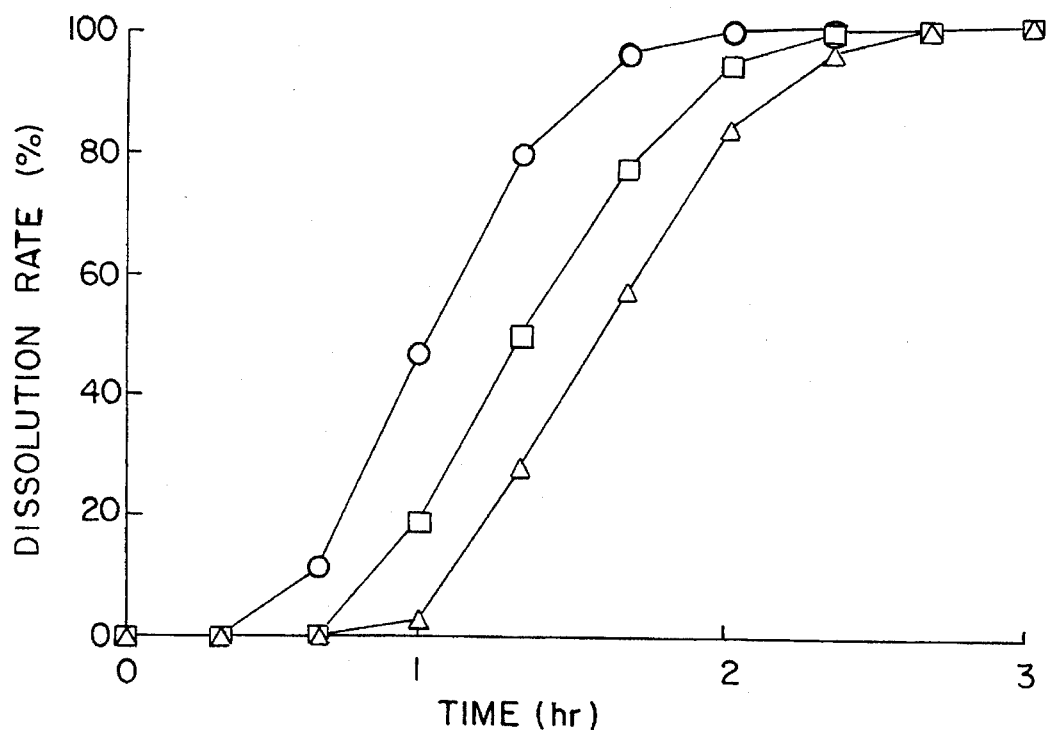
FIG. 6 is a graph showing the results of dissolution tests carried out in Test Example 6 using the controlled release-initiation and controlled release-rate pharmaceutical compositions obtained in Example 6.

As is apparent from FIG. 6, each of the inventive pharmaceutical compositions releases trapidil quickly after a lag time, and the lag time becomes longer as the coating ratio increases, thus showing that the release-starting time can be changed at will.

EXAMPLE 7

A 400 g portion of phenylpropanolamine hydrochloride was mixed with 800 g of corn starch and pulverized into fine powder. While spraying a solution of 40 g of hydroxypropyl cellulose dissolved in 760 g of ethyl alcohol, 1,280 g of the fine powder was applied to 400 g of Nonpareil 103 (spherical sugar having a particle size of 500 to 710 μm, manufactured by Freund Industrial Co., Ltd.) to effect rolling granulation, followed by 5 hours of drying at 60° C. The resulting granules were treated with screens and those which passed through a 12 mesh screen (sieve opening, 1.41 mm) but not a 32 mesh screen (sieve opening, 0.50 mm) were collected as uncoated granules.

Next, 1,000 g of the uncoated granules thus obtained were put in a fluidized bed coating apparatus and sprayed with a coating solution composed of 8% hydroxypropylmethyl cellulose, 2% talc, 45% ethyl alcohol and 45% purified water until a 10% increase in the weight of the uncoated granules was attained. In this way, central cores of the present invention were obtained.

Thereafter, 250 g of the thus obtained central cores were put in a fluidized bed coating apparatus and sprayed with a coating solution composed of 12% Eudragit RS, 8% dimethylpolysiloxane, 4% light anhydrous silicic acid, 1% glycerine fatty acid ester and 75% ethyl alcohol until a 40% (Example 7-1), an 80% (Example 7-2) or a 120% (Example 7-3) increase in the weight of the granules was attained. In this way, the controlled release-initiation and controlled release-rate pharmaceutical compositions of the present invention were obtained in a dosage form of granules.

TEST EXAMPLE 7

Dissolution of phenylpropanolamine hydrochloride from the controlled release-initiation and controlled release-rate pharmaceutical compositions 7-1, 7-2 and 7-3 of the present invention obtained in Example 7 was measured in the same manner as described in Test Example 1. The results are shown in FIG. 7.

Figure 7:
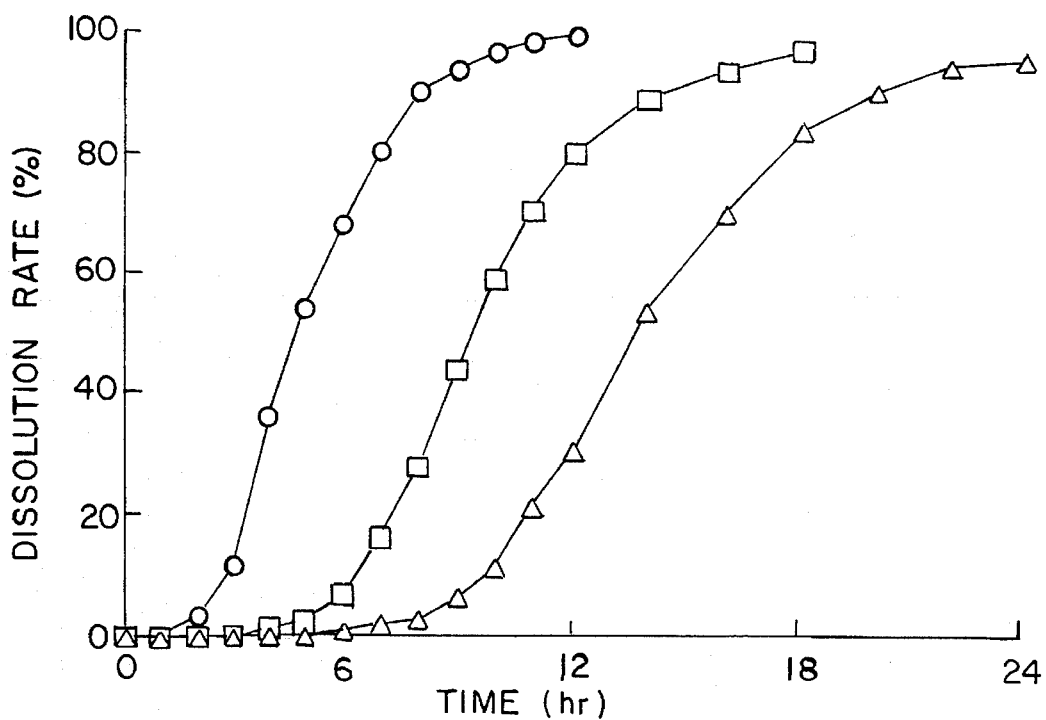
FIG. 7 is a graph showing the results of dissolution tests carried out in Test Example 7 using the controlled release-initiation and controlled release-rate pharmaceutical compositions obtained in Example 7.

As is apparent from FIG. 7, each of the inventive pharmaceutical compositions releases phenylpropanolamine hydrochloride quickly after a lag time, and the lag time becomes longer as the coating ratio increases. In addition, the release of phenylpropanolamine hydrochloride after lag time occurs at the same rate independent of the coating ratio.

EXAMPLE 8

Central cores containing trapidil were obtained in the same manner as described in Example 1.

Thereafter, 250 g of the thus obtained central cores were put in a fluidized bed coating apparatus and sprayed with a coating solution composed of 12.5% Eudragit RS, 5% dimethylpolysiloxane, 6.25% talc, 1.25% glycerine fatty acid ester and 75% ethyl alcohol until a 40% (Example 8-1) or a 65% (Example 8-2) increase in the weight of the granules was attained. In this way, the controlled release-initiation and controlled release-rate pharmaceutical compositions of the present invention were obtained in a dosage form of granules.

TEST EXAMPLE 8

Dissolution of trapidil from the controlled release-initiation and controlled release-rate pharmaceutical compositions 8-1 and 8-2 of the present invention obtained in Example 8 was measured in the same manner as described in Test Example 1. The results are shown in FIG. 8.

Figure 8:
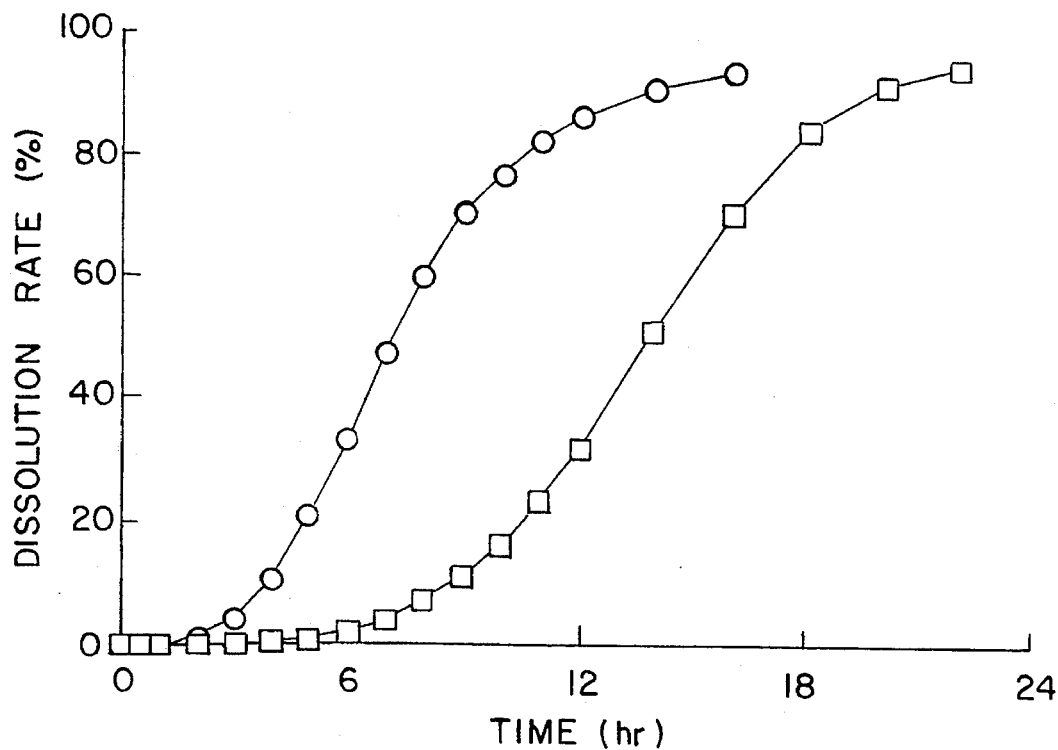
FIG. 8 is a graph showing the results of dissolution tests carried out in Test Example 8 using the controlled release-initiation and controlled release-rate pharmaceutical compositions obtained in Example 8.

As is apparent from FIG. 8, each of the inventive pharmaceutical compositions releases trapidil quickly after a lag time, and the lag time becomes longer as the coating ratio increases, thus showing that the release-starting time can be changed at will.

EXAMPLE 9

A 150 g portion of diclofenac sodium salt was mixed with 1,295 g of corn starch and pulverized into a fine powder. While spraying a solution of 33 g of hydroxypropyl cellulose dissolved in 627 g of ethyl alcohol, 1,051 g of the fine powder was applied to 400 g of Nonpareil 103 (spherical sugar having a particle size of 500 to 710 μm, manufactured by Freund Industrial Co., Ltd.) to effect rolling granulation, followed by 4 hours of drying at 60° C. The resulting granules were treated with screens and those which passed through a 14 mesh screen (sieve opening, 1.19 mm) but not a 32 mesh screen (sieve opening, 0.50 mm) were collected as central cores.

Thereafter, 500 g of the thus obtained central cores were put in a fluidized bed coating apparatus and sprayed with a coating solution composed of 12% Eudragit RS, 8% dimethylpolysiloxane, 4% light anhydrous silicic acid, 1% glycerine fatty acid ester and 75% ethyl alcohol until an 80% increase in the weight of the granules was attained (Example 9-1). In this way, the controlled release-initiation and controlled release-rate pharmaceutical composition 9-1 of the present invention was obtained in a dosage form of granules.

TEST EXAMPLE 9

Dissolution of trapidil from the controlled release-initiation and controlled release-rate pharmaceutical composition 9-1 of the present invention obtained in Example 9 was measured in the same manner as described in Test Example 1. The results are shown in FIG. 9.

Figure 9:
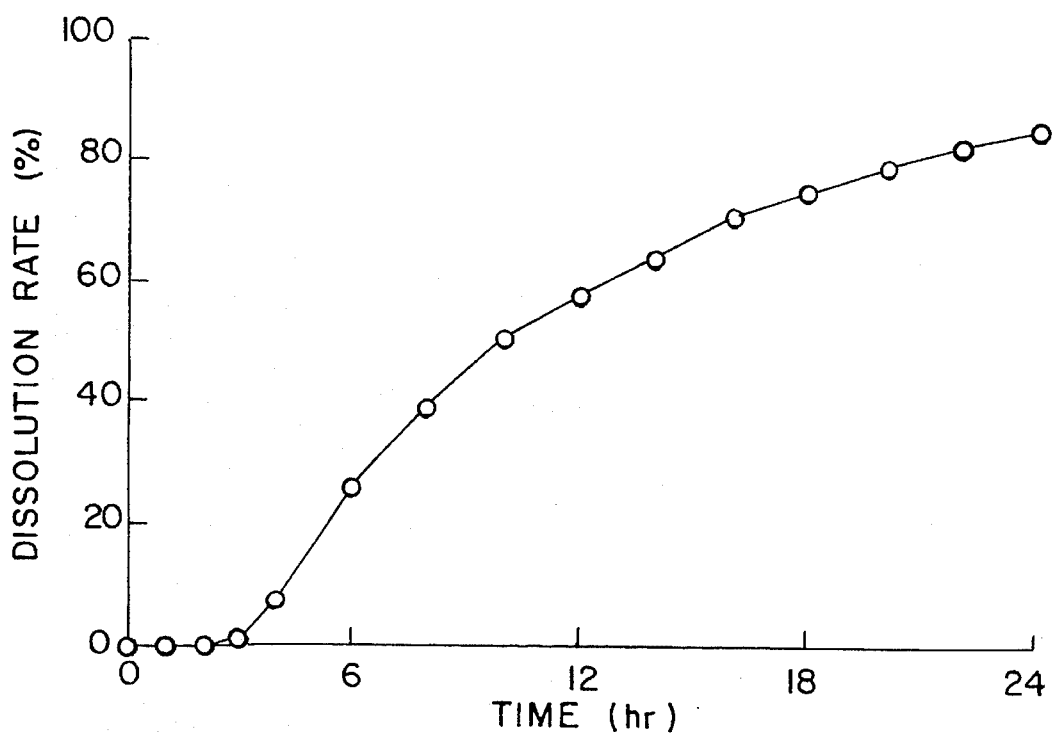
FIG. 9 is a graph showing the result of a dissolution test carried out in Test Example 9 using the controlled release-initiation and controlled release-rate pharmaceutical composition obtained in Example 9.

As is apparent from FIG. 9, the inventive pharmaceutical composition releases diclofenac sodium salt after 4 hours of lag time.

EXAMPLE 10

Central cores containing trapidil were obtained in the same manner as described in Example 1.

Thereafter, 250 g of the thus obtained central cores were put in a fluidized bed coating apparatus and sprayed with a coating solution composed of 6.75% ethyl cellulose, 0.45% polyvinyl pyrrolidone, 4.8% dimethylpolysiloxane, 2.4% light anhydrous silicic acid, 0.6% glycerine fatty acid ester and 85% ethyl alcohol until a 70% increase in the weight of the granules was attained (Example 10-1). In this way, the controlled release-initiation and controlled release-rate pharmaceutical composition of the present invention was obtained in a dosage form of granules.

TEST EXAMPLE 10

Dissolution of trapidil from the controlled release-initiation and controlled release-rate pharmaceutical composition 10-1 of the present invention obtained in Example 10 was measured in the same manner as described in Test Example 1. The results are shown in FIG. 10.

Figure 10:
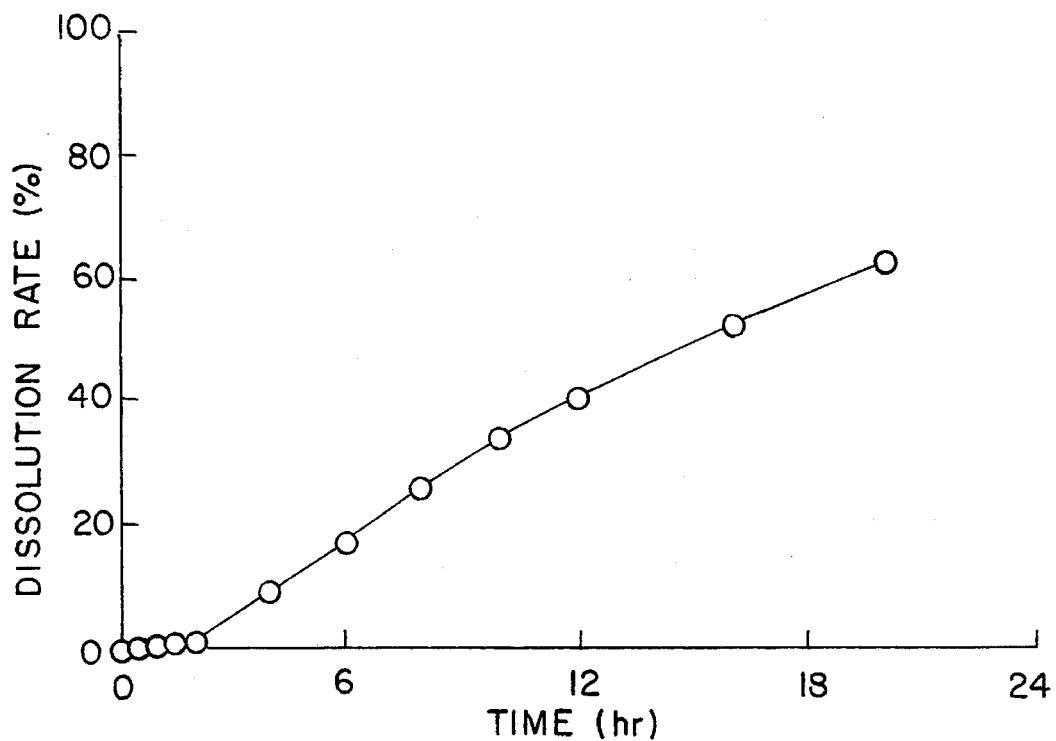
FIG. 10 is a graph showing the result of a dissolution test carried out in Test Example 10 using the controlled release-initiation and controlled release-rate pharmaceutical composition obtained in Example 10.

As is apparent from FIG. 10, the controlled release-initiation and controlled release-rate pharmaceutical composition of the present invention releases trapidil quickly after a lag time.

EXAMPLE 11

Central cores containing trapidil were obtained in the same manner as described in Example 1.

Thereafter, 250 g of the thus obtained central cores were put in a fluidized bed coating apparatus and sprayed with a coating solution composed of 12% Eudragit S100, 8% dimethylpolysiloxane, 4% light anhydrous silicic acid, 1% glycerine fatty acid ester and 75% ethyl alcohol until a 100% increase in the weight of the granules was attained (Example 11-1). In this way, the controlled release-initiation and controlled release-rate pharmaceutical composition of the present invention was obtained in a dosage form of granules.

TEST EXAMPLE 11

Dissolution of trapidil from the controlled release-initiation and controlled release-rate pharmaceutical composition 11-1 of the present invention obtained in Example 11 was measured in the same manner as described in Test Example 1. The results are shown in FIG. 11.

Figure 11:
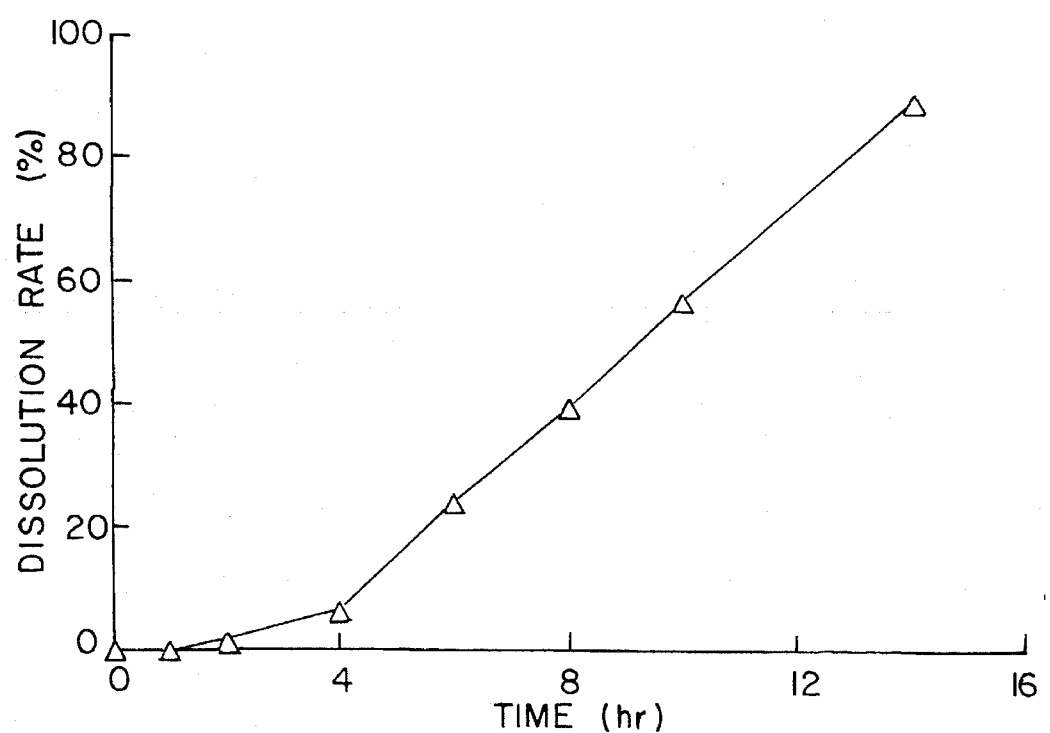
FIG. 11 is a graph showing the result of a dissolution test carried out in Test Example 11 using the controlled release-initiation and controlled release-rate pharmaceutical composition obtained in Example 11.

As is apparent from FIG. 11, the controlled release-initiation and controlled release-rate pharmaceutical composition of the present invention releases trapidil quickly after a lag time.

EXAMPLE 12

A 900 g portion of theophylline was mixed with 100 g of talc and pulverized into fine powder. While spraying a solution of 20 g of hydroxypropyl cellulose dissolved in 380 g of ethyl alcohol, 800 g of the fine powder was applied to 200 g of Nonpareil 103 (spherical sugar having a particle size of 500 to 710 mm, manufactured by Freund Industrial Co., Ltd.) to effect rolling granulation, followed by 3 hours of drying at 60° C. The resulting granules were treated with screens and those which passed through a 14 mesh screen (sieve opening, 1.19 mm) but not a 32 mesh screen (sieve opening, 0.50 mm) were collected as central cores.

Thereafter, 400 g of the thus obtained uncoated granules were put in a fluidized bed coating apparatus and sprayed with a coating solution composed of 12% Eudragit RS, 8% dimethylpolysiloxane, 4% light anhydrous silicic acid, 1% glycerine fatty acid ester and 75% ethyl alcohol until a 25% increase in the weight of the uncoated granules was attained. In this way, the controlled release-initiation and controlled release-rate pharmaceutical composition of the present invention was obtained in a dosage form of granules.

EXAMPLE 13

A 500 g portion of pranoprofen was mixed with 500 g of microcrystalline cellulose, and the mixture was kneaded by adding 200 g of purified water, made into granules by extrusion granulation using a 0.8 mm screen and then treated with Marumerizer. After 5 hours of drying at 60° C., the resulting granules were treated with screens and those which passed through a 14 mesh screen (sieve opening, 1.19 mm) but not a 32 mesh screen (sieve opening, 0.50 mm) were collected as uncoated granules.

Thereafter, 500 g of the thus obtained uncoated granules were put in a fluidized bed coating apparatus and sprayed with a coating solution composed of 14% Eudragit RS, 7% dimethylpolysiloxane, 3% light anhydrous silicic acid, 1% glycerine fatty acid ester and 75% ethyl alcohol until a 50% increase in the weight of the uncoated granules was attained. In this way, a controlled release-initiation and controlled release-rate pharmaceutical composition of the present invention was obtained in a dosage form of granules.

EXAMPLE 14

A mixture consisting of 100 g chlorpheniramine maleate, 400 g microcrystalline cellulose, 490 g lactose and 10 g magnesium stearate was applied to a tablet machine to obtain uncoated tablets (80 mg/tablet) as central cores.

Thereafter, 500 g of the thus obtained central cores were put in a coating pan and sprayed with a coating solution composed of 7.5% Eudragit RS, 3% dimethylpolysiloxane, 1.5% light anhydrous silicic acid, 0.5% glycerine fatty acid ester and 87.5% ethyl alcohol until the weight of each tablet was increased to 10 mg. In this way, the controlled release-initiation and controlled release-rate pharmaceutical composition of the present invention was obtained in a dosage form of tablets.

COMPARATIVE EXAMPLE 2

Central cores containing trapidil were obtained in the same manner as described in Example 1.

Thereafter, 250 g of the thus obtained central cores were put in a fluidized bed. coating apparatus and sprayed with a coating solution composed of 12% Eudragit RS, 4% light anhydrous silicic acid, 1% glycerine fatty acid ester, 8% corn oil and 75% ethyl alcohol until a 60% (Comparative Example 2-1) or 90% (Comparative Example 2-2) increase in the weight of the granules was attained. In this way, comparative pharmaceutical compositions in which silicone in the coating membrane was replaced by corn oil were obtained in a dosage form of granules.

TEST EXAMPLE 12

Dissolution of trapidil from the comparative pharmaceutical compositions 2-1 and 2-2 obtained in Comparative Example 2, in which silicone in the coating membrane was replaced by corn oil, was measured in the same manner as described in Test Example 1. The results are shown in FIG. 12, together with the results of the controlled release-initiation and controlled release-rate pharmaceutical compositions 1-1 and 1-2 of the present invention obtained in Example 1.

Figure 12:
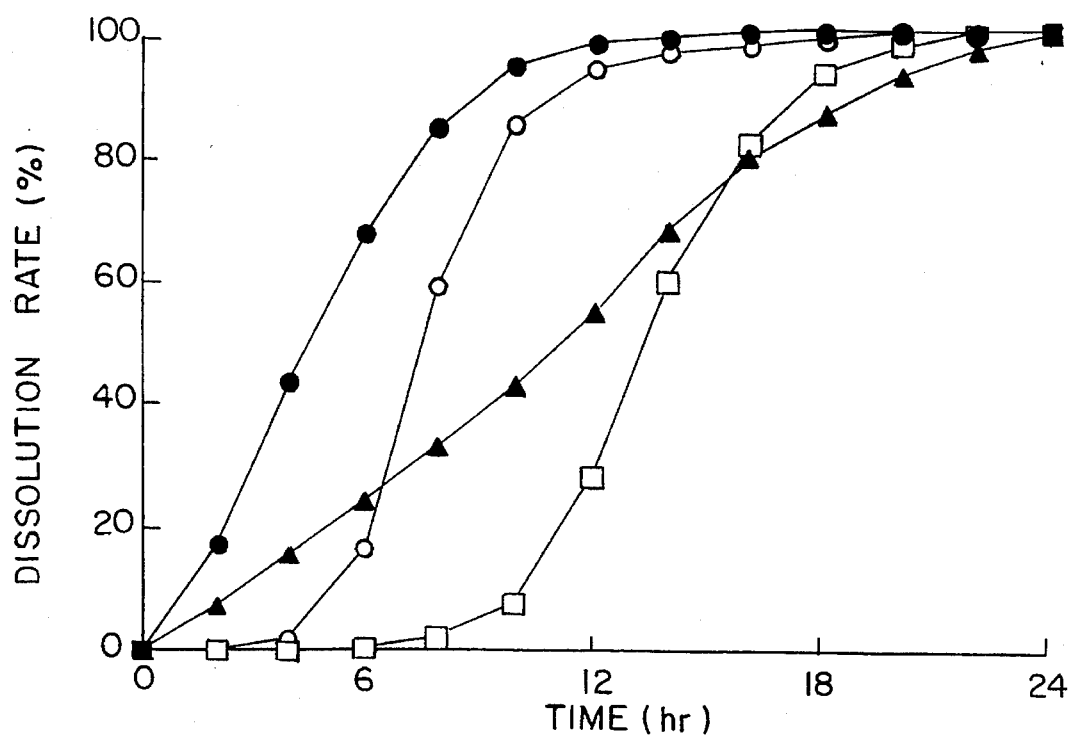
FIG. 12 is a graph showing the results of dissolution tests carried out in Test Example 12 using the controlled release-initiation and controlled release-rate pharmaceutical compositions obtained in Example 1 and comparative preparations obtained in Comparative Example 2.

As is apparent from FIG. 12, the lag time prior to the commencement of drug-releasing cannot be obtained in the corn oil-applied comparative pharmaceutical compositions.

COMPARATIVE EXAMPLE 3

Central cores containing trapidil were obtained in the same manner as described in Example 1.

Thereafter, 250 g of the thus obtained central cores were put in a fluidized bed coating apparatus and sprayed with a coating solution composed of 12% Eudragit RS, 4% light anhydrous silicic acid, 1% glycerine fatty acid ester, 8% liquid paraffin and 75% ethyl alcohol until a 60% (Comparative Example 3-1) or a 90% (Comparative Example 3-2) increase in the weight of the granules was ,attained. In this way, comparative pharmaceutical compositions in which silicone in the coating membrane was replaced by liquid paraffin were obtained in a dosage form of granules.

TEST EXAMPLE 13

Dissolution of trapidil from the comparative pharmaceutical compositions 3-1 and 3-2 obtained in Comparative Example 3, in which silicone in the coating membrane was replaced by liquid paraffin, was measured in the same manner as described in Test Example 1. The results are shown in FIG. 13, together with the results of the controlled release-initiation and controlled release-rate pharmaceutical compositions 1-1 and 1-2 of the present invention obtained in Example 1.

Figure 13:
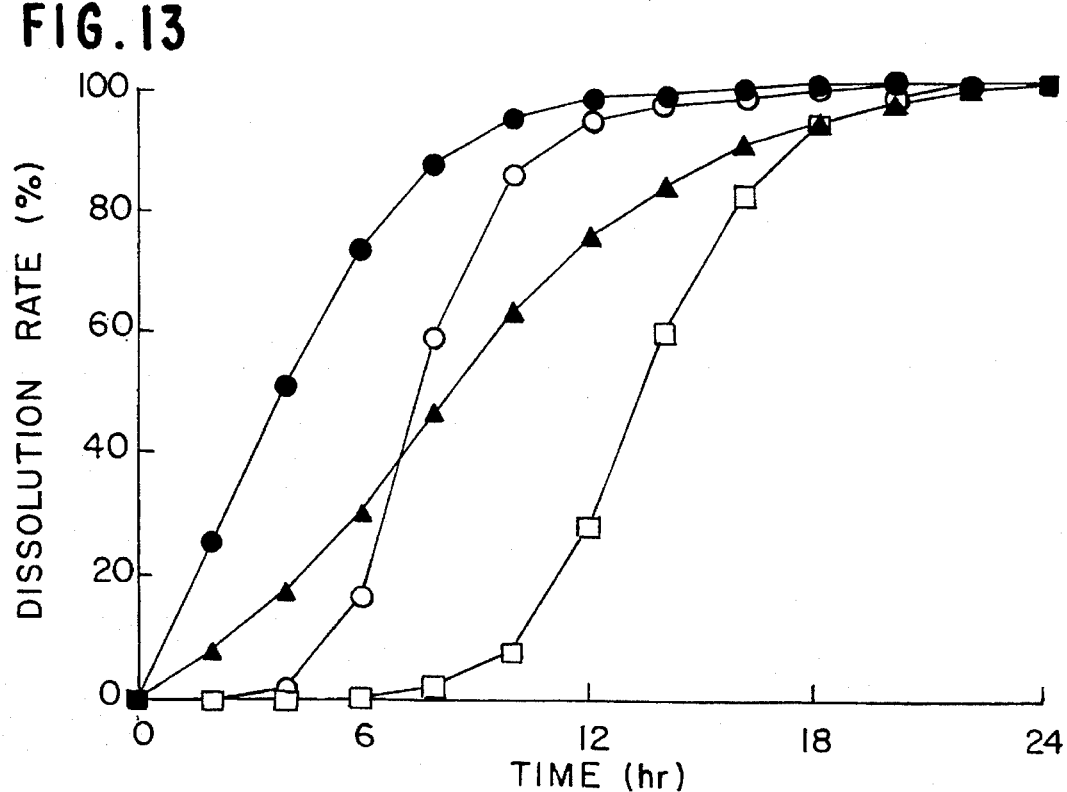
FIG. 13 is a graph showing the results of dissolution tests carried out in Test Example 13 using the controlled release-initiation and controlled release-rate pharmaceutical compositions obtained in Example 1 and comparative preparations obtained in Comparative Example 3.

As is apparent from FIG. 13, the lag time prior to the commencement of drug-releasing cannot be obtained in the liquid paraffin-applied comparative pharmaceutical compositions.

While the invention has been described in detail and with reference to specific examples thereof, it will be apparent to one skilled in the art that various changes and modifications can be made therein without departing from the spirit and scope thereof.

What is claimed is:

1. A controlled release-initiation and controlled release-rate pharmaceutical composition comprising a drug-containing composition coated with a membrane layer comprising a water insoluble polymer and at least 5% by weight of a silicone, based on the weight of the water insoluble polymer.

2. The controlled release-initiation and controlled release-rate pharmaceutical composition as claimed in claim 1, wherein said water insoluble polymer is at least one compound selected from the group consisting of ethyl acrylate/ methyl methacrylate/ethyl trimethylammonium chloride methacrylate terpolymer, ethyl cellulose and an enteric polymer.

3. The controlled release-initiation and controlled release-rate pharmaceutical composition as claimed in claim 2, wherein said enteric polymer is methacrylic acid/ethyl acrylate copolymer, methacrylic acid/methyl methacrylate copolymer, hydroxypropylmethylcellulose phthalate, hydroxypropylmethylcellulose acetate succinate, carboxymethylethyl cellulose or cellulose acetate phthalate.

4. The controlled release-initiation and controlled release-rate pharmaceutical composition as claimed in claim 1, wherein said silicone is a silicone resin or a silicone oil.

5. The controlled release-initiation and controlled release-rate pharmaceutical composition as claimed in claim 1, wherein said membrane layer contains a silicone hold carrier.

6. The controlled release-initiation and controlled release-rate pharmaceutical composition as claimed in claim 1, wherein said drug-containing composition comprises a therapeutically-effective amount of a drug and a pharmaceutically acceptable carrier.

7. The controlled release-initiation and controlled release-rate pharmaceutical composition as claimed in claim 1, wherein said membrane layer is present in an amount of from 2% to 200% based on the weight of the drug-containing composition, said water insoluble polymer is present in an amount of from 20% to 95% by weight based on the total weight of the membrane layer, and said silicone is present in an amount of from 5% to 200% by weight based on the weight of the water insoluble polymer.

8. The controlled release-initiation and controlled release-rate pharmaceutical composition as claimed in claim 1, wherein said membrane layer further comprises a water soluble polymer.

9. The controlled release-initiation and controlled release-rate pharmaceutical composition as claimed in claim 8, wherein said water soluble polymer is selected from the group consisting of hydroxypropylmethyl cellulose, hydroxypropyl cellulose, polyvinyl pyrrolidone and polyethylene glycol.

10. The controlled release-initiation and controlled release-rate pharmaceutical composition as claimed in claim 2, wherein said water insoluble polymer is ethyl acrylate/ methyl methacrylate/ethyl trimethylammonium chloride methacrylate terpolymer.

11. The controlled release-initiation and controlled release-rate pharmaceutical composition as claimed in claim 10, wherein said terpolymer has an ethyl acrylate/methyl methacrylate/ethyl trimethylammonium chloride methacrylate weight ratio of from 1:2:0.1 to 1:2:0.2.

12. The controlled release-initiation and controlled release-rate pharmaceutical composition as claimed in claim 4, wherein said silicone is dimethylpolysiloxane.

13. The controlled release-initiation and controlled release-rate pharmaceutical composition as claimed in claim 5, wherein said silicone hold carrier is selected from the group consisting of talc, light anhydrous silicic acid, microcrystalline cellulose and starch.

14. A method for administering a time-released drug comprising the step of:

administering a therapeutically-effective amount of a drug-containing composition coated with a membrane layer comprising a water insoluble polymer and at least 5% by weight of a silicone, based on the weight of the water insoluble polymer, to a person in need of such a drug-containing composition.

15. The method for administering a time-released drug as claimed in claim 14, wherein the starting time at which the drug is to be released is controlled by the thickness of the membrane layer, and the rate at which the drug is to be released is controlled by the composition of the membrane layer.

16. The method for administering a time-released drug as claimed in claim 14, wherein the membrane layer is used in an amount of 2% to 200% by weight based on the drug-containing composition weight.

17. The method for administering a time-released drug as claimed in claim 14, wherein the water insoluble polymer is at least one compound selected from the group consisting of ethyl acrylate/methyl methacrylate/ethyl trimethylammonium chloride methacrylate terpolymer, ethyl cellulose and an enteric polymer.

18. The method for administering a time-released drug as claimed in claim 17, wherein said enteric polymer is methacrylic acid/ethyl acrylate copolymer, methacrylic acid/methyl methacrylate copolymer, hydroxypropylmethylcellulose phthalate, hydroxypropylmethylcellulose acetate succinate, carboxymethylethyl cellulose or cellulose acetate phthalate.

19. The method for administering a time-released drug as claimed in claim 14, wherein said silicone is a silicone resin or a silicone oil.

20. The method for administering a time-released drug as claimed in claim 14, wherein the membrane further comprises a silicone hold carrier.

21. The controlled release-initiation and controlled release-rate pharmaceutical composition as claimed in claim 1, wherein the silicone is present in an amount of 5 to 200% by weight based on the weight of the water insoluble polymer.

22. The method for administering a time-released drug as claimed in claim 14, wherein the silicone is present in an amount of 5 to 200% by weight based on the weight of the water insoluble polymer.

* * * * *